(12) United States Patent
Pederson, Jr. et al.

(10) Patent No.: US 6,432,080 B2
(45) Date of Patent: *Aug. 13, 2002

(54) STENT SECUREMENT BY BALLOON MODIFICATION

(75) Inventors: Gary J. Pederson, Jr.; Jan D. Seppala, both of Maple Grove; Scott M. Hanson, Columbia Heights, all of MN (US)

(73) Assignee: Scimed Life Systems, INC, Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/898,741

(22) Filed: Jul. 3, 2001

Related U.S. Application Data

(63) Continuation of application No. 09/335,361, filed on Jun. 17, 1999, now Pat. No. 6,280,412.

(51) Int. Cl.[7] .......................... A61M 29/00; A61F 11/00
(52) U.S. Cl. ................... 604/103.07; 606/108
(58) Field of Search .................... 604/96.01, 103.06, 604/103.07, 103.08, 915, 916, 101.01, 101.05; 606/108, 191–195; 623/1.11, 1.12

(56) References Cited

U.S. PATENT DOCUMENTS

| | | | |
|---|---|---|---|
| 4,950,227 A | 8/1990 | Savin et al. ................ 604/8 |
| 5,158,548 A | 10/1992 | Lau et al. ................ 604/96 |
| 5,445,646 A | 8/1995 | Euteneuer ................ 606/198 |
| 5,571,135 A | 11/1996 | Fraser et al. ................ 606/108 |
| 5,989,280 A | 11/1999 | Euteneuer ................ 606/198 |
| 6,059,813 A | 5/2000 | Vrba et al. ................ 606/198 |
| 6,238,410 B1 | 5/2001 | Vrba et al. ................ 606/198 |
| 6,280,412 B1 | 8/2001 | Pederson et al. |

OTHER PUBLICATIONS

U.S. patent application Ser. No. 09/711,687, Vrba et al., filed Nov. 10, 2000.

U.S. patent application Ser. No. 09/369,918, Euteneuer et al., filed Aug. 6, 1999.

U.S. patent application Ser. No. 09/451,405, Eutenuer et al., filed Nov. 30, 1999.

Primary Examiner—Sharon Kennedy
(74) Attorney, Agent, or Firm—Vidas, Arrett & Steinkraus, PA.

(57) ABSTRACT

Improved stent securement in a balloon catheter including balloon modification. The improvement comprises a circumferential fold in at least one of the distal cone portion and proximal cone portion over a portion of the body portion. The fold includes first and second layers of balloon material which are touching each other in a plurality of locations. The fold encompasses a circumferential end portion of the stent for securing it in place until dilation of the balloon.

10 Claims, 3 Drawing Sheets

STENT SECUREMENT BY BALLOON MODIFICATION

CROSS REFERENCE TO RELATED APPLICATIONS

This application is a Continuation application of application Ser. No. 09/335,361, filed Jun. 17, 1999, issued as U.S. Pat. No. 6,280,412 B1 on Aug. 28, 2001, the contents of which are hereby incorporated by reference.

BACKGROUND OF THE INVENTION

This invention relates to improved apparatus suitable for stent delivery and implantation.

Stents are implantable devices which are placed within body lumens and the like, such as blood vessels. Stents are typically tubular in form, the diameter of which can be increased for implantation. They maybe made of plastic or metal. Stents are usually introduced for implantation percutaneously by means of a catheter and the diameter of the stent is increased by inflation of a balloon on the catheter.

In one aspect, this invention relates to an improvement in the stent delivery system described in U.S. Pat. No. 4,950,227 to Savin et al., entitled "Stent Delivery System" and issued on Aug. 21, 1990. This patent is incorporated herein in its entirety by reference.

That patent discloses a stent delivery system in which a catheter carries, on its distal end portion, a stent which is held in place around the catheter prior to and during percutaneous delivery by means of one and preferably two sleeves. The sleeves are positioned around the catheter with one end portion attached thereto and overlap an end portion (s) of the stent to hold it in place on the catheter in a contracted condition. Each sleeve is elastomeric in nature so as to stretch and release the stent when it expands for implantation. The stent is expandable by means of the expandable balloon on the catheter.

SUMMARY OF THE INVENTION

In a first aspect, this invention provides securement of a stent on a balloon by means of a folded or rolled end portion of the balloon itself.

In another aspect of this invention the balloon configured as described above is used in combination with the elastic sleeves of the Savin et al. patent.

Additionally, the balloon shape may be modified, as by enlarged cone portions, to facilitate the above improvements.

Moreover, these features may be used alone or in combination and may be applied to one or both ends of the stent to secure it for delivery.

BRIEF DESCRIPTION OF THE DRAWING(S)

DESCRIPTION OF THE PREFERRED EMBODIMENTS

Figure 1:
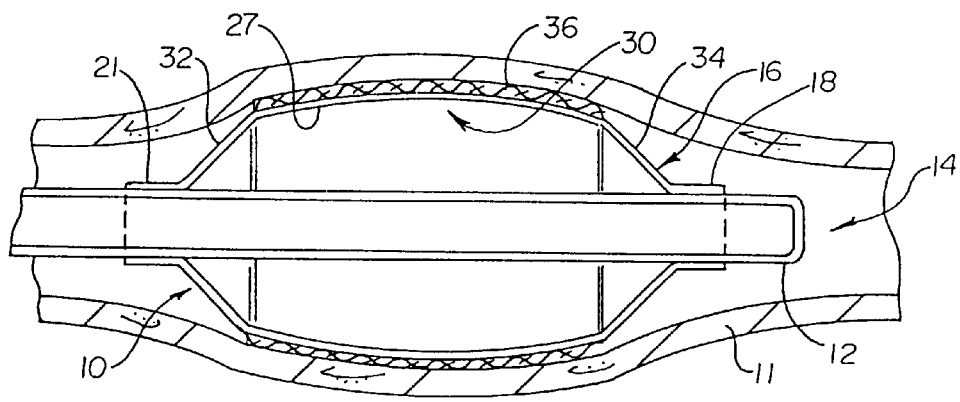
FIG. 1 is an axial cross-section view of one embodiment of a balloon catheter of the present invention, showing the catheter operatively disposed in a body conduit.

A stent-carrying balloon catheter is illustrated generally in FIG. 1 and designated by the reference numeral 10. The catheter 10 is operatively disposed in a body conduit defined by walls 1 1 and includes an elongate cannula 12 having a distal end 14 and a proximal end (not shown).

Catheter 10 includes a balloon 16 (inflated) having a distal end wall 18 and a proximal end wall 21. A central wall 27 is disposed between end wall 18 and 21 in a central region 30 of balloon 16.

In this embodiment the end walls 18 and 21 are relatively thick and relatively small in diameter. This is in comparison to central wall 27 of balloon 16 which is relatively thin and relatively large in diameter.

A pair of transition walls or cones 32 and 34 are of particular interest to the preferred embodiment of this invention. A stent 36 is shown on balloon 16 being expanded by the dilated balloon.

Figure 2:
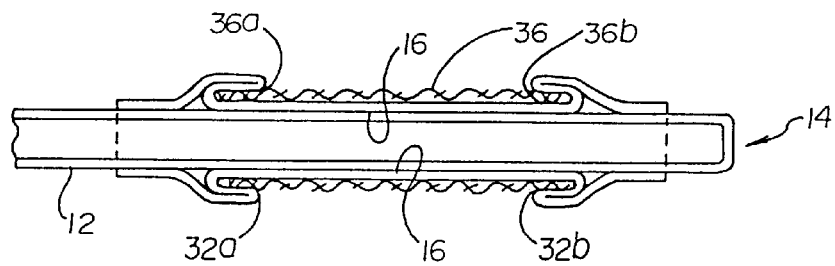
FIG. 2 is an axial cross-section view of a balloon catheter, the balloon being rolled or folded onto the catheter cannula to encompass the ends of the stent carried by the balloon.
Figure 3:
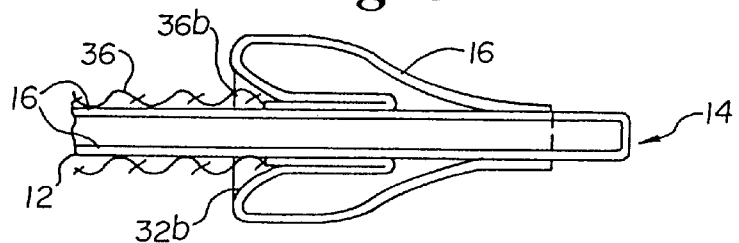
FIG. 3 is an enlarged cross-section view of one end of the balloon of FIG. 2.

Referring to FIGS. 2 and 3, the cones 32 and 34 of particular interest are discussed in more detail. As can be seen in the Figures, cone portions 32 and 34 are rolled or folded as at 32a and 32b under or over themselves and the catheter cannula 12 to encompass the ends 36a and 36b respectively of the stent thus securing it to the catheter.

Upon inflation of balloon 16, folds 32a and 32b open to a configuration similar to that shown in FIG. 1 to release the stent for expansion by the balloon.

Figure 4:
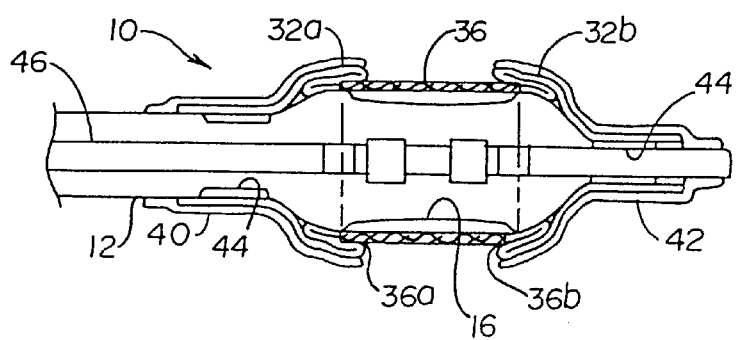
FIG. 4 is a schematic plane view of the distal end portion of a balloon catheter having a stent fixed to the catheter by means of folds in the balloon and retractable sleeves.
Figure 5:
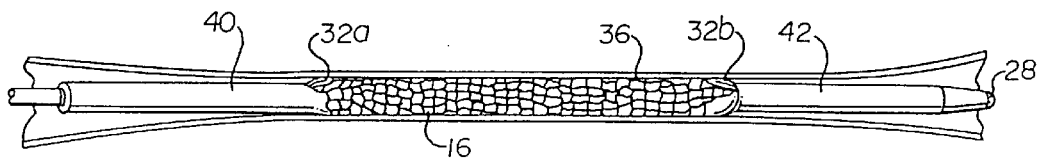
FIGS. 5, 6, 7 and 8 are schematic views showing simultaneous expansion of a catheter balloon and stent and the resultant release of the stent from the balloon and retaining sleeves.

Referring to FIG. 4, a stent delivery system 10 includes a balloon catheter 12 having a balloon 16 fixed to the catheter for remote inflation as is known in the art. The catheter includes an elongate cannula 46 and may include marker bands 44. Balloon 16 is shown in a somewhat contracted state. A stent 36 is positioned about balloon 16 on catheter 12 and held by two overlying retaining sleeves, a proximal one 40 and a distal one 42.

Stent 36 may be of any known type. In this instance for example it may be a balloon expandable stent of stainless steel, such as the known types which are cut or etched from hypotubes.

Sleeves 40 and 42 may be axially fixed along catheter 12 as by an adhesive (not shown). The sleeves overlap stent 36 at each of the stent ends or margin 36a and 36b as shown. Additionally, further securement of stent 36 is provided by balloon folds 32a and 32b similar to those shown in FIGS. 2 and 3.

Sleeves 40 and 42 are comprised of elastomeric polymeric material such as rubber, urethane, styrenes, silicone, polyurethane, polyethylene, PET, ABS and polyimides. A lubricant additive such as silicone may be included in or on the sleeves. Additionally, further securement of stent 16 is provided by balloon folds 32a and 32b similar to those shown in FIGS. 2 and 3.

Figure 6:
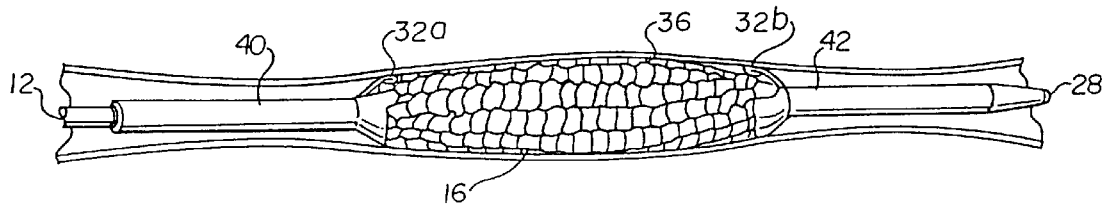
Figure 7:
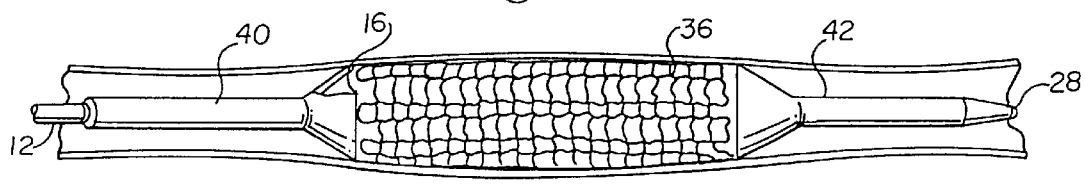
Figure 8:
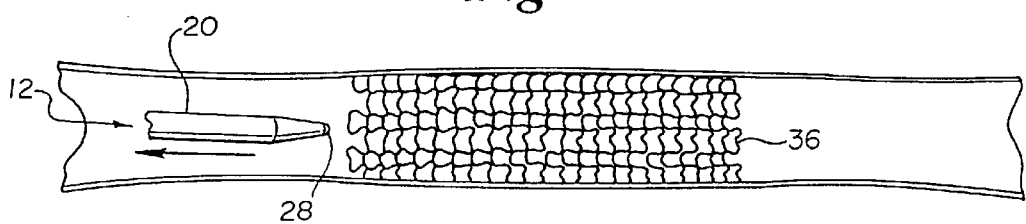

Referring to FIGS. 5, 6, 7 and 8, the stent delivery system 10 of FIG. 4 is inserted percutaneously by known technique into a body lumen or the like. As the stent is positioned (FIG. 2), balloon 16 is expanded (FIGS. 6 and 7). During balloon expansion, stent 36 is also expanded and sleeves 40 and 42 deform elastically while balloon folds 32a and 32b open to release the stent. The balloon is then deflated by standard technique and catheter 12 with sleeves 40 and 42 is axially removed leaving stent 36 implanted (FIG. 8).

In some instances, only one sleeve may be provided at one end in the system. Also, only one fold may be provided in the balloon at one end. Preferably, the fold(s) are in the end regions of the balloon but could be located anywhere to accommodate the size stent used relative to the balloon length used.

Figure 9:
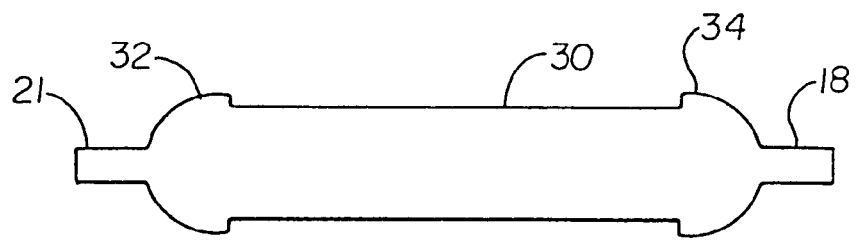
FIG. 9 is a schematic showing of a balloon of modified construction according to the invention.

Referring now to FIG. 9, a balloon 16 of modified construction according to the invention is shown. Balloon 16 includes a central body portion 30 of a nominal size, distal catheter attachment ends 18 and 21, and cone portions 32 and 34, also in end regions of the balloon. Cone portions 32 and 34 are larger in diameter, at least adjacent to their attachment to body 30, than the nominal body 30 size.

Figure 10:
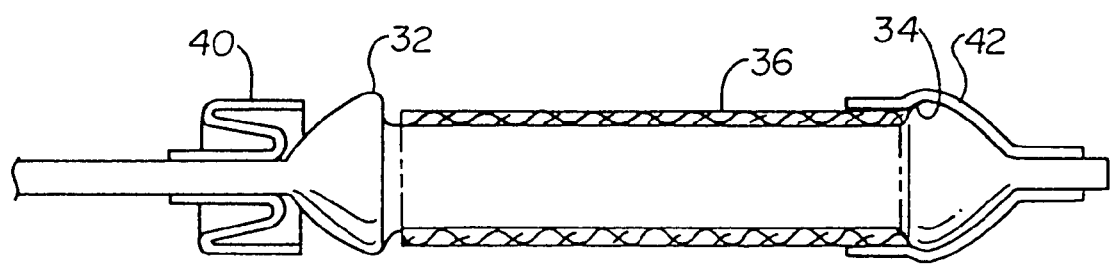
FIG. 10 is an axial cross-section similar to FIG. 1 showing the balloon of FIG. 9 on a catheter with retractable sleeves.

A purpose of this construction modification in the balloon is to facilitate sleeve retraction as is shown in FIG. 10. As can be seen from the Figure, when balloon 30 begins to inflate, the enlarged cones 32 and 34 increase in size to aid in sleeve 40 and 42 retraction to expose the stent 36 for expansion upon further inflation of the balloon.

It is contemplated within the purview of this invention that the balloon, particularly in the region of the cones, may be physically modified so as to change the mechanical characteristics of the balloon in order to facilitate folding of the balloon. For example, this may be accomplished by forming slits or other apertures in those regions of the balloon. Sealing would be accomplished by the balloon fold or by covering by the sleeves. Such apertures might be formed in the balloon as made or formed in it later. For example, when the stent is crimped to the balloon, the stent ends maybe utilized to form apertures in the balloon material.

Figure 11:
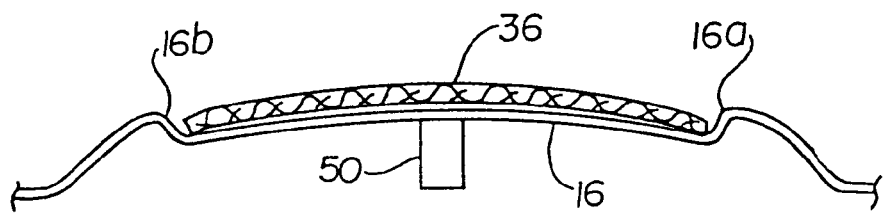
FIG. 11 is a schematic view in fragment of another embodiment of the invention.

Referring now to FIG. 11, which is a fragment schematic of a catheter system similar to those of the preceding Figures, a modified balloon construction is shown in which the stent 36 is positioned within a raised end 16a and 16b of balloon 16. Optionally, a dam 50 may be included as is known in the art. The balloon will preferably include raised end portions at both ends as shown. However, only one end, preferably the distal end 16a, could be raised. The raised relationship may be slitted by forming it in the balloon similar to the construction shown in FIG. 9. Rotating sleeves may be optionally used in this embodiment.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. In a stent-carrying balloon catheter in which a balloon is positioned within a stent for expanding the stent upon dilation of the balloon, the balloon comprising a body portion positioned between a distal cone portion and a proximal cone portion, the improvement comprising a circumferential fold in at least one of the distal cone portion and proximal cone portion over a portion of the body portion, the fold including first and second layers of balloon material which are touching each other in a plurality of locations, the fold encompassing a circumferential end portion of the stent for securing it in place until dilation of the balloon.

2. The improvement of claim 1 in which there are two folds in the balloon one each in the region of the proximal cone portion and the distal cone portion of the balloon.

3. The improvement of claim 2 in which the two folds in the balloon each encompassing an end respectively of the stent.

4. A catheter for delivering an expandable medical device to a body lumen, the catheter comprising:

an expandable balloon, the balloon defining a stent mounting region for retaining a stent until dilatation of the balloon, the balloon comprising a body portion positioned between a distal cone portion and a proximal cone portion, the stent being disposed in an unexpanded state about at least the body portion of the balloon, at least one of the distal cone portion and proximal cone portion comprising a circumferential fold of balloon material, the circumferential fold, the circumferential fold encompassing a circumferential end portion of the stent for securing it in place until dilation of the balloon.

5. The catheter of claim 4 wherein, at least a portion of at least one of the proximal cone portion and distal cone portion have a larger diameter respectively adjacent to the body portion than the diameter of the body portion in that adjacent region.

6. The catheter of claim 4 wherein the distal cone portion comprises a distal circumferential fold of balloon material for securing the stent in place until dilation of the balloon, and the proximal cone portion comprises a proximal circumferential fold of balloon material for securing the stent in place until dilatation of the balloon.

7. The catheter of claim 4 wherein the body portion of the balloon comprises a body wall having a body wall thickness, the distal cone portion of the balloon comprises a distal cone wall having a distal cone wall thickness, and the proximal cone portion of the balloon comprises a proximal cone wall having a proximal cone wall thickness, at least one of the proximal cone wall thickness and the distal cone wall thickness being thicker than the body wall thickness.

8. The catheter of claim 4 wherein the circumferential fold comprises first and second layers of balloon material which are touching each other in a plurality of locations.

9. The catheter of claim 4 further comprising at least one elastomeric sleeve, the at least one elastomeric sleeve carried in the region of the balloon and positioned around the catheter, the at least one elastomeric sleeve having a first end attached to the catheter and a second end lying over at least the end portion of the circumferential end portion of the stent, the at least one elastomeric sleeve retaining at least the circumferential end portion of the stent to the stent mounting region when the stent is in the unexpanded state, at least the second end of the at least one elastomeric sleeve being retracted from the at least the circumferential end portion of the stent when the balloon and stent are expanded respectively to an expanded state.

10. The catheter of claim 9 wherein the at least one elastomeric sleeve and the circumferential fold being cooperatively engaged to the circumferential end portion of the stent to retain the stent in the unexpanded state prior to expansion of the balloon.

\* \* \* \* \*